(12) United States Patent
Warden et al.

(10) Patent No.: US 10,017,306 B2
(45) Date of Patent: *Jul. 10, 2018

(54) TAMPER RESISTANT ASSEMBLY FOR SECURING VALUABLE MATERIAL

(71) Applicant: Synthetic Genomics, Inc., La Jolla, CA (US)

(72) Inventors: Laurence Warden, Poway, CA (US); Tei Newman-Lehman, San Diego, CA (US); Daniel G. Gibson, Carlsbad, CA (US)

(73) Assignee: Synthetic Genomics, Inc., La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/682,288

(22) Filed: Aug. 21, 2017

(65) Prior Publication Data

US 2017/0341834 A1    Nov. 30, 2017

Related U.S. Application Data

(63) Continuation of application No. 14/702,378, filed on May 1, 2015, now Pat. No. 9,751,668.

(Continued)

(51) Int. Cl.
*G01N 21/00* (2006.01)
*B65D 61/00* (2006.01)
(Continued)

(52) U.S. Cl.
CPC .......... *B65D 61/00* (2013.01); *B01L 3/50851* (2013.01); *B65B 5/04* (2013.01);
(Continued)

(58) Field of Classification Search
CPC .. G02B 3/0056; G02B 27/2214; G02B 27/60; G02B 1/00; G02B 1/002; G02B 5/1857;
(Continued)

(56) References Cited

U.S. PATENT DOCUMENTS 4,825,801 A * 5/1989 Weber .................. G09F 3/0376
                                                   116/201
5,042,842 A    8/1991 Green et al.
(Continued)

FOREIGN PATENT DOCUMENTS

JP          5447168 B2     3/2014

OTHER PUBLICATIONS

International Search Report dated Aug. 12, 2015, regarding PCT/US2015/028778.
Supplementary European Search Report dated Nov. 6, 2017, regarding EP 15 78 6364.8.

*Primary Examiner* — Michael P Stafira
(74) *Attorney, Agent, or Firm* — DLA Piper LLP (US)

(57) ABSTRACT

The invention provides a tamper resistant assembly that that securely contains a valuable material. The assembly has a container for holding the valuable material, an optional carrier that contains the container, one or more cover components that enclose the valuable material in the container, and one or more labels having a plurality of devices that reveal tampering by distortion of at least one of the plurality of devices. The label(s) are positioned so that dislodging a cover component causes a detectable distortion in at least one of the plurality of devices, thereby revealing tampering with the assembly. In one embodiment the label can be affixed partially to a surface of a cover component and partially to a surface of the container or the optional carrier. Also disclosed are methods of detecting tampering and method of manufacturing a temper-resistant assembly. Because the assembly allows a remote validator to validate the assembly prior to providing essential instructions or authorization for conducting procedures on valuable material contained by the assembly, the manufacturer is assured that its procedures are being provided only to authorized persons.

31 Claims, 3 Drawing Sheets

Related U.S. Application Data (60) Provisional application No. 61/988,045, filed on May 2, 2014.

(51) Int. Cl.
| | |
|---|---|
| *B65D 43/02* | (2006.01) |
| *B01L 3/00* | (2006.01) |
| *B65B 7/28* | (2006.01) |
| *G01N 21/64* | (2006.01) |
| *B65B 5/04* | (2006.01) |
| *B65D 25/10* | (2006.01) |
| *B65D 25/20* | (2006.01) |
| *B65C 1/04* | (2006.01) |
| *G01N 21/77* | (2006.01) |
| *B01L 9/00* | (2006.01) |

(52) U.S. Cl.
CPC .............. *B65B 7/28* (2013.01); *B65C 1/04* (2013.01); *B65D 25/108* (2013.01); *B65D 25/205* (2013.01); *B65D 43/0235* (2013.01); *G01N 21/6428* (2013.01); *G01N 21/6486* (2013.01); *B01L 9/523* (2013.01); *B01L 2200/026* (2013.01); *B01L 2200/028* (2013.01); *B01L 2200/0689* (2013.01); *B01L 2200/141* (2013.01); *B01L 2300/0829* (2013.01); *B01L 2300/0887* (2013.01); *B65D 2101/0007* (2013.01); *B65D 2101/0092* (2013.01); *G01N 21/77* (2013.01); *G01N 2021/6439* (2013.01)

(58) Field of Classification Search
CPC ........ G02B 5/1861; G02B 5/23; G01N 27/22; G01N 21/6408; G01N 21/6428
See application file for complete search history.

(56) References Cited

U.S. PATENT DOCUMENTS

| | | | |
|---|---|---|---|
| 5,312,680 A * | 5/1994 | Simpson | B65D 27/30 206/807 |
| 5,411,295 A | 5/1995 | Bates et al. | |
| 5,605,230 A | 2/1997 | Marino, Jr. et al. | |
| 5,605,738 A * | 2/1997 | McGinness | B41M 3/144 250/365 |
| 5,629,093 A | 5/1997 | Bischof et al. | |
| 5,683,774 A | 11/1997 | Faykish et al. | |
| 5,718,859 A * | 2/1998 | Frederiksen | A61J 1/1412 156/211 |
| 5,770,283 A | 6/1998 | Gosselin et al. | |
| 6,632,403 B1 * | 10/2003 | Barmore | B65D 33/34 206/223 |
| 7,098,792 B1 * | 8/2006 | Ahlf | G08B 13/1427 235/492 |
| 7,995,196 B1 * | 8/2011 | Fraser | G06K 9/00577 356/71 |
| 8,123,126 B2 * | 2/2012 | Balinsky | G06K 9/00577 235/380 |
| 8,171,567 B1 | 5/2012 | Fraser et al. | |
| 8,371,051 B2 | 2/2013 | Wu | |
| 8,512,857 B2 | 8/2013 | Lawrence et al. | |
| 2001/0035261 A1 | 11/2001 | Banahan | |
| 2008/0219885 A1 * | 9/2008 | Horstman | A61B 10/0096 422/400 |
| 2011/0132788 A1 * | 6/2011 | Middlesworth | B65D 71/0092 206/459.5 |
| 2013/0345071 A1 | 12/2013 | Drmanac | |
| 2014/0017659 A1 * | 1/2014 | Steinman | A01N 1/0247 435/1.2 |
| 2014/0099024 A1 * | 4/2014 | Remer | G06K 9/78 382/165 |
| 2014/0346072 A1 * | 11/2014 | Jacobson | A61B 50/31 206/438 |

\* cited by examiner

TAMPER RESISTANT ASSEMBLY FOR SECURING VALUABLE MATERIAL

CROSS-REFERENCE TO RELATED APPLICATIONS

This application is a continuation application of U.S. application Ser. No. 14/702,378, now pending; which claims the benefit under 35 USC § 119(e) to U.S. Application Ser. No. 61/988,045 filed May 2, 2014. The disclosure of each of the prior applications is considered part of and is incorporated by reference in the disclosure of this application.

BACKGROUND OF THE INVENTION

Valuable materials include those for which a great deal of time and precision has been expended for their production. Manufacturers and providers of such materials have always been desirous a methods of protecting those materials and ensuring that they are not vulnerable to copying, counterfeiting, or unauthorized use. There is therefore a continuing need for devices and methods for securing such valuable materials. This need has expanded to include the need for producers to ensure that proprietary products manufactured are not tampered with or opened, and therefore subjected to counterfeiting or unauthorized use, after the manufacturing and sale process is complete. Manufacturers have sometimes sought to satisfy at least some of these needs by resorting to particular designs of tamper evident labels, which typically utilize a detectable pattern or frangible liner that is secured with an adhesive to thereby prevent tampering and counterfeiting. More robust forms of tamper resistance are described in U.S. Pat. No. 7,098,792, which uses a circuit based sensor sensitive to reveal tampering and US 2001/0035261, which combines a fluorescent taggant with an optically variable image. These devices utilize a visual inspection to reveal tampering. This inspection is typically performed by the end user and authorization or validation by the producer is not typically available with these methods and devices. Presently, there are no devices or methods available that utilize a mated set of components with multiple mechanical and visual features that ensure that authorized products sold have not been tampered with or subject to counterfeiting, and which also allow the producer to authorize or validate the products at the point of use.

There is therefore a need for an automated way to detect if a manufactured product containing valuable materials has been opened, tampered with or is otherwise counterfeit, which can occur during transportation or storage of the manufactured device. There is also a need for manufacturers to have a method of validating or authorizing the use of materials that have an origin at a facility under their control.

SUMMARY OF THE INVENTION

The present invention provides a tamper resistant assembly that that securely contains a valuable material. The assembly has a container for holding the valuable material, one or more cover components that enclose the valuable material in the container, optionally a carrier that contains the container, and one or more labels having a plurality of devices that reveal tampering by a detectable distortion of at least one of the plurality of devices. The one or more labels are positioned so that any attempts to open the container and access the valuable material contained inside will cause distortion in one or more of the plurality of devices or features in the label(s), and such distortion is detectable by a detection system (e.g., an optical detection system) and/or a remote validator. If such distortion is detected authorization can be withheld or the issuance of instructions for performing a method on the valuable material can be denied by the party controlling the remote validator. Because the assembly allows for a remote validator to validate the assembly prior to providing the authorization and/or instructions for conducting procedures on the material, the manufacturer is assured that its materials and procedures are being provided only to validly purchased materials and for authorized uses.

In a first aspect the invention provides a tamper resistant assembly that securely contains a valuable material. The assembly has a container for holding the valuable material and, optionally, a carrier comprising the container; one or more cover components that enclose(s) the valuable material in the container; one or more labels comprising a plurality of devices that reveal tampering by distortion of at least one of the plurality of devices, the one or more labels positioned so that dislodging one or more of the one or more cover components causes the distortion of at least one of the plurality of devices. The distortion is detectable by a detection system and tampering with the assembly is revealed. The label can be affixed partially to a surface of a cover component, and partially to a surface of the container or to the optional carrier comprising the container. In various embodiments the detection system of the assembly can be an optical detection system, and the distortion can be detectable by a remote validator. The label can have multiple layers, which can have the plurality of devices. The plurality of devices can be selected from one or more of: a pattern detectable under light of a first range of wavelengths, a pattern or substance detectable under light of a second range of wavelengths, a pattern detectable under light of a third range of wavelengths, a frangible layer, a pattern detectable under visible light, a pattern detectable under infra-red light, a taggant ink detectable under ultra-violet light, a barcode, a hologram, and an RFID label.

In some embodiments the assembly has a carrier that contains the container and the label is affixed partially to a surface of a cover component and partially to a surface of the carrier comprising the container. The label can have a device detectable under visible light, a device detectable under infra-red light, and a device detectable under ultra-violet light when the label is distorted. The label can have a frangible layer that is distorted upon application of shear forces and also have a pattern detectable in visible light present on the frangible layer. The distortion can be distortion of the pattern detectable under visible light.

The label can have a layer that has a pattern that is detectable under infra-red light, and/or a taggant ink that is detectable under ultra-violet light when the label is distorted to expose the taggant ink but is not detectable when the label is intact. In some embodiments the label has a first layer that with a pattern detectable under visible light and a second layer with a pattern detectable under infra-red light, and the second layer is present on top of the first layer.

In some embodiments the container of the assembly is a multi-well plate. One or more of the cover component(s) can seal the valuable material in the container, and the valuable material can be fragments of nucleic acid that, when joined in a particular order, comprise a larger desired sequence of nucleic acid. The fragments of nucleic acid can be randomly placed in a plurality of individual compartments or wells of the container. In another embodiment the valuable material is situated in individual compartments or wells of the container and one or more of the wells also has one or more taggant inks.

In another aspect the invention provides a method of detecting the occurrence of tampering with an assembly containing a valuable material. The method involves analyzing assembly of the invention as described herein with a detection system, and detecting the presence or absence of distortion in one or more of the plurality of devices and thereby detecting whether tampering with the assembly has occurred. The detection of the distortion can be communicated to a remote validator, which can be a computer that receives information about the detection of distortion in one or more of the plurality of devices, or information about the absence of distortion in the plurality of devices. The methods can also involve a step of removing one or more cover components and detecting the presence or absence of one or more taggant inks detectable at a specific wavelength or range of wavelengths in one or more of the individual compartments or wells.

In another aspect the invention provides a method of manufacturing a tamper resistant assembly that securely contains a valuable material. The method involves placing the valuable material in a container that is, optionally, comprised by a carrier; placing one or more cover components on the container; positioning one or more labels of the invention as described herein so that dislodging at least one cover component causes distortion in at least one label, the distortion detectable by a detection system as described herein. The positioning can involve affixing the one or more labels partially to a surface of the one or more cover components and partially to a surface of the container or the optional carrier that comprises the container. The methods also can involve placing one or more taggant inks detectable at a specific wavelength or range of wavelengths in one or more individual compartments of the container.

These and other objects, aspects, and features of the invention will become more fully apparent to those of ordinary skill in the art upon review of the following detailed description of the invention and the claims in conjunction with the accompanying figures.

DETAILED DESCRIPTION OF THE INVENTION

The present invention provides distinct advantages over existing technology for securing valuable materials and ensuring that they are not tampered with or counterfeited. The invention allows a producer of valuable materials to validate or authorize the materials prior to activity at the point of use. The invention is also useful in any application where the origin of materials must be verified. The invention provides an assembly for containing a valuable material that utilizes a design and a label having multiple devices that reveal tampering by distortion of at least one of the devices in the label. With such an assembly one is able to achieve a highly increased level of security for a valuable product. In a particular embodiment it was found that by specifically ordering the devices within the label, one is able to incorporate a maximum number of devices and a resulting increase in security.

Figure 1:
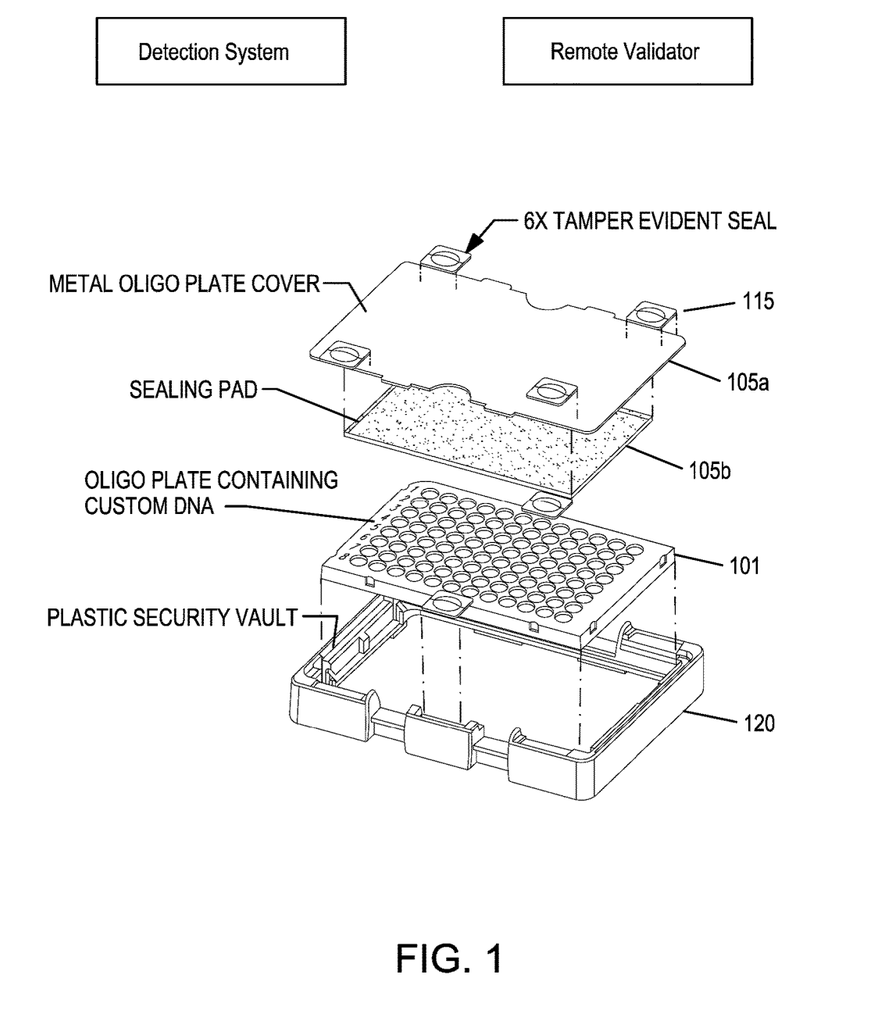
FIG. 1 provides an exploded view of a tamper resistant assembly of the invention. This embodiment has a carrier and two cover components 105.

FIG. 1 provides an exploded diagram of an embodiment of an assembly of the invention, showing its component parts. In this embodiment the assembly has a separate carrier, but in other embodiments the carrier can be combined with the container into a single component, or eliminated entirely. The container 101 is situated securely within the carrier component 120.

The container 101 has one or more cover components 105, which are secured on the container. The cover or cover components can have several purposes. In various examples the cover or cover components is/are that part of the assembly that prevents access to the materials in the container without first removing or dislodging one or more cover components and thereby cause a distortion in at least one of the plurality of devices in the one or more labels. The cover or cover components can also serve to protect the materials in the container. The assembly can have one or more cover components that comprise the cover. While FIG. 1 depicts the cover 105 as having two components (a cover piece 105a and a sealing pad 105b), in different embodiments the cover has one or two or three or more than three components as desired for the specific application. In various embodiments the cover components 105 can include a cover piece 105a, one or more sealing pads 105b, layers, or membranes (e.g., a foil sealing cover) that seal the materials within the container and prevent them from drying out or otherwise being lost or adulterated, and can also serve as a protective layer for the container. Other cover components (not shown) can be included in additional embodiments, and some cover components can be eliminated, depending on the convenience of the application. The cover piece 105a, sealing pad 105b, thermally conductive pad 105c (shown in FIG. 3), adhesive film 105d (shown in FIG. 3), layers, or membranes, when present as one or more separate components, are considered as components that together comprise the cover 105. Thus, in various embodiments the label can be affixed partially to a surface of the container and partially to a surface of any one or more cover components that may be present in the embodiment, e.g., partially to the surface of the container and partially to a surface of a sealing pad; or partially to the surface of the container and partially to a surface of a sealing layer; or partially to the surface of the container and partially to a surface of a sealing membrane, or partially to a cover piece and partially to the container and/or carrier. In each case it is considered as being partially affixed to the cover because the cover includes any of the cover components, as the term is used herein. In another embodiment of the assembly the label is not affixed to the container but instead is affixed partially to two or more components of the cover, i.e., partially to at least two of any of the cover piece, sealing pad, sealing layer, sealing membrane, or whatever other cover component may be included in the embodiment. The one or more cover components enclose the valuable material in the container and while it is desirable that at least one component of the cover actually seal the valuable materials in the container, this is not a requirement, but it is desirable that at least one component of the cover substantially seal or protect the valuable materials in the container. By enclosing the valuable material is meant that the valuable material does not escape the container even upon inversion of the container and/or assembly.

In yet another embodiment the label is affixed to any one or two or more components of the assembly in a manner so that the valuable materials in the container cannot be accessed without causing a distortion of at least one of the plurality of devices in at least one label.

In still another embodiment the labels are positioned so that dislodging one or more cover component(s) causes a distortion to occur in at least one of the plurality of devices in the label(s). In a particular embodiment one or more labels are affixed to separate surfaces of the container and/or carrier. In these embodiments the label(s) envelop one or more cover components of the assembly so that the one or more cover components cannot be removed from the assembly and/or materials in the container cannot be accessed without causing distortion in at least one of the plurality of devices in the label. In some of these embodiments the labels are not affixed to a cover component but rather to two separate areas of the container or two areas of the carrier or at least one area of the container and at least one area of the carrier, or to two areas of the cover, and can envelop or wrap around the container and/or one or more cover components. In still other embodiments two or more areas of the label are affixed to each other so that the label envelops the assembly partially or completely (e.g., in the shape of a loop), thus rendering it impossible to dislodge the one or more cover components without causing a distortion in the label. The assembly can then be shaped so that the one or more cover components cannot be dislodged and access to the valuable materials gained without causing a distortion in at least one layer of at least one label. By dislodge is meant movement of a cover component so that access is gained to the valuable materials inside the container.

When more than one cover component (e.g., sealing pad, layer, or membrane) is present they can also serve a reinforcing function. In some embodiments the cover includes a sealing cover or sealing pad made of foil or another suitable material, and no plastic or metal or other part need be present to form the cover. In FIG. 1 there are also depicted labels 115 (4 shown), which are shown as being partially affixed to a cover piece 105*a*. Another portion of the labels 115 can be affixed to a surface of the container or another cover component or the carrier (when present) when the assembly is assembled, so that none of the labels 115 can be removed, and thus allow the cover to be removed or dislodged and access gained to the materials inside the container without causing a distortion in one or more of the devices in one or more of the labels 115. There is no limit to the shape or number of labels that can be provided with the assembly as the invention accommodates a wide variety of shapes and numbers of labels, and the number of labels is at least one. The cover components of the container can be made of any suitable material, e.g., plastic or metal. In different embodiments the cover can also be connected to the container or to a carrier (when present), or to both. In different embodiments the cover can be movable about a hinge, or can partially or completely slide off the container to provide access to the valuable materials. When the cover is a foil seal, it can be simply peeled back when the container is ready for use and can be validated or authorized before or after such peeling.

Figure 3:
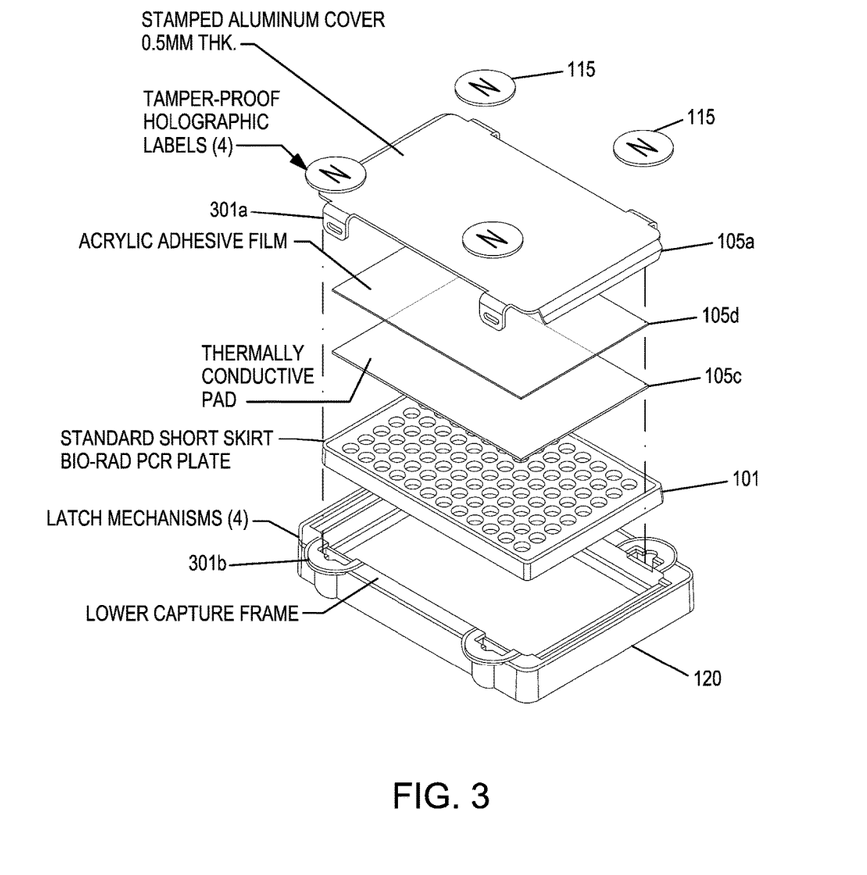
FIG. 3 provides an exploded view of a tamper resistant assembly of the invention. This embodiment has a carrier and latches that are used to secure the cover component(s) to the carrier. The container is contained in the carrier.

In another embodiment one or more cover components can have one or more latches 301 or holding mechanisms that lock or snap the cover onto the container, as depicted in FIG. 3. The embodiment depicted in FIG. 3 has a carrier 120 or lower capture frame and a container 101 and there are depicted three cover components 105, but it is understood the assembly can have one or two or three or more than three cover components. In these embodiments cover component 105*c* is a thermally conductive pad, cover component 105*d* is an acrylic adhesive film, and cover component 105*a* is a stamped aluminum cover piece. Other cover components can be included and the cover components can be made of any suitable material for the purpose of the component such as, for example, foil or plastic or metals. Component 301*a* is a portion of a latch, which fits snugly into latch portion 301*b*, which is present on the carrier. During manufacturing and after the assembly has been assembled one or more of the label(s) can be situated on or over the latch, thus preventing the cover component 105*a* from being removed without causing distortion of at least one of the plurality of devices present in one or more layers of the label. In one embodiment the latches 301 can be disengaged by a key on an instrument that has previously performed the detection of the occurrence of tampering with the assembly.

Container

The containers utilized in the assemblies of the invention can be any container that can hold a valuable material. In particular embodiments the container is a biological plate or multi-well plate (e.g., a multi-well or 96 well plate) containing DNA or another material for biological applications. But in other applications the containers can have any internal volume and any number of individual compartments or wells of appropriate volume for the application is useful. Examples of additional valuable materials include, but are not limited to, amino acids, peptides, proteins, RNA, or a reagent or mixture of reagents for conducting a procedure, method, or assay. But any valuable material, whether biological or inorganic, can be contained in the container.

Carrier

The carrier is an optional component, which can provide a secure seat or holder for the container and to allow the cover to be placed on top of the container so that one or more labels can be affixed to prevent access to the valuable materials without causing distortion in at least one of the plurality of devices in the label(s) (e.g., partially to a cover component and partially to a surface of the container or to a carrier containing the container). In some embodiments the carrier and container can be comprised as a single component or unit. In other embodiments the carrier can be a separate component from the container and can take the form of plastic or other suitable material, into which the container fits securely or is otherwise held, and that allows for the cover to be placed on the container. The carrier can be designed so that it interacts with the cover piece or another cover component and provides a convenient location for one or more of the labels to be positioned. The carrier can also be sized and shaped to allow the assembly to fit securely and conveniently onto an instrument that performs validation or authorization or otherwise performs a procedure on the valuable materials in the container. In some embodiments the cover and carrier can also be comprised as a single unit or all of the cover, carrier and container can be comprised as a single unit made of any suitable material. The precise form or arrangement of these components is not critical, and any configuration or form of components allowing for these purposes will be suitable in the invention.

Label

The label can be positioned so that dislodging one or more of the cover components causes a distortion to occur in at least one of the plurality of devices in the label(s). In some embodiments the label is affixed to one or more components of the assembly so that the valuable material in the container cannot be accessed without causing distortion in at least one of the plurality of devices in a label. "Access" refers to the ability to manipulate materials in the container, or remove materials from, or add materials to the container. In some embodiments the label is affixed partially to a surface of a cover component and partially to a surface of the container or a carrier comprising the container, so that the label cannot be removed without causing distortion in at least one of the devices in the label. The label contains one or more layers or plies having at least one device that becomes distorted in a detectable way if the assembly is tampered with, for example by attempting to remove or manipulate the label and gain access to the material in the container. In some embodiments each layer of the label has a device and will serve a different purpose and the various layers will combine to fulfill the objectives of the label of the invention. While is it desirable for the label(s) to have a plurality of incorporated devices in some embodiments the label(s) can have a single device as described herein. In some embodiments the assembly can utilize multiple labels, each having one or more of the devices that reveal tampering, as described herein. In one embodiment the assembly has multiple labels and the labels can comprise a different type of device described herein.

In various embodiments the label has one layer or multiple layers. Examples of layers include, but are not limited to, one or more of 1) a layer that has frangible properties, e.g., a layer that has a web of semi-elastic thermoplastic or that has a metallic foil or that has flexible tabs built into the layer; 2) a layer printed with a taggant ink that is detectable under light of one or more first specific wavelength(s) or range(s) of wavelengths (e.g., of the uv spectrum); 3) a layer that has a pattern that is detectable under light of one or more second specific wavelength(s) or range(s) of wavelengths (e.g., the visible spectrum); and/or 4) a pattern that is detectable under light of one or more third specific wavelength(s) or range(s) of wavelengths (e.g., infra-red spectrum). A pattern detectable under light of one wavelength or range of wavelengths (e.g., the visible spectrum) can be present in a layer on or near the upper surface of the label, and a pattern detectable under light of another wavelength or range of wavelengths (e.g., infra-red spectrum) can be printed on the opposite side of the same layer, or on another layer. The label can also have a tensioned layer that covers all or a part of a layer having a taggant ink. In addition to these layers the label can have one or more adhesive layers in between and/or above and/or below these layers for the purpose of assembling the label and/or providing a layer to adhere to one or more cover components, container, or carrier. In certain embodiments the bottom of the label is that side affixed to the container and carrier or cover, and the top of the label can be considered the opposite side of the label. The label can also contain a top layer which can be a transparent layer that protects the label and covers the label. Therefore not every layer of the label must contain a device that reveals tampering. In other embodiments the label can have additional layers, for example layers with printing detectable at a fourth wavelength or range(s) of wavelength(s)) or can have some combination of these layers. Any of the layers and any combination of the layers can be comprised in the label. In the invention the taggant ink is not necessarily one that is detectable under ultra-violet light and other appropriate taggant inks can also be used in the invention.

The cutting of the label can be used to add a further layer of security to the method of detecting tampering. The label can be cut by a component of the instrument that performs the validation, or by a separate instrument, or even by hand. The label can be sized and shaped so that the force of the cutting instrument is directed towards a specific area of the label to ensure a cut that exposes a taggant ink present at one layer of the label. As the label is cut the taggant ink becomes exposed to the detector, and the ability to detect the presence of the taggant ink is therefore further confirmation that the assembly is valid (i.e., its source is an authorized, legally appropriate provider). Authorization refers to the acknowledgment by a legally appropriate provider (either directly or through one or more third parties) that an assembly is valid.

Plurality of Devices

The label(s) can contain one device or a plurality of devices that would reveal if tampering with the assembly had occurred. A number of devices can be provided in the label for this purpose, and a label can have one or more of these devices incorporated within each layer of the label. Examples include, but are not limited to a frangible layer, a pattern detectable under light of one or more first wavelength(s) or range(s) of wavelengths (e.g., visible light), a taggant ink detectable under light of one or more second wavelength(s) or range of wavelengths (e.g., ultra-violet light), a pattern detectable under light of one or more third wavelength(s) or range of wavelengths (e.g., infra-red light), a barcode, a hologram, and an RFID label. Other types of devices that can be incorporated into the label will also be realized. In some embodiments more than one device can be incorporated into the same layer of the label. The label can also have layers that are simply adhesive layers. These layers may therefore not have any device but rather are present to form adhesive layers for adhering the layers to one another or to the container and/or cover and/or carrier. The labels are not limited to any particular number of layers and any number of layers or patterns can be used, which can be detectable under any convenient number of types or wavelengths of light. Any suitable one or more wavelength(s) or range(s) of wavelengths of light can be used. In different examples the ranges of wavelengths include from about 390 to about 700 nm, or from about 450 to about 650 nm; or less than 400 nm or from about 10 nm to about 400 nm or from about 100 nm to about 350 nm; or from about 700 nm to about 1 mm or from about 750 to about 950 nm or greater than 700 nm.

The frangible layer of the label is designed to be easily distorted or fragmented when subjected to mechanical stress or shear forces. It can be made of a material that fragments or otherwise becomes irreversibly changed in a detectable manner after being subjected to mechanical stress and cannot resume its prior configuration. Examples of materials that can be used for this layer of the label include, but are not limited to, biaxially oriented polypropylene, PET, lacquered paper, PVC, latex, rubber, thermoplastic urethane, or a material with a thin wax layer. But the person of ordinary skill with resort to this disclosure will realize a number of other frangible materials that will find use in the invention. This can also be a tensioned layer and can be a stretched material so that distortion in this layer results in a detectable loss of the configuration of the layer and tampering is revealed.

A layer of the label can serve to cover all or part of a lower layer that is printed with one or more taggant inks (detectable under uv light) and therefore render all or part of the taggant ink(s) unable to be detected because of the covering layer. This covering layer can be a tensioned layer, e.g., a web of semi-elastic thermoplastic that is tensioned prior to lamination. It can also be a layer of metallic foil (e.g., aluminum), or web that is cut in a particular pattern to create a series of flexible tabs. Upon being subject to distortion the layer contracts due to release of the tension, thus becoming smaller and exposing the taggant ink below it.

Another layer of the label can be made of a material that will have a pattern on the surface that is detectable under visible light, for example by an optical detector. The pattern can be a printed pattern. This layer can also be made of an opaque or a semi-opaque material. In some embodiments this layer can also have printed on the underside or opposite side of the layer a pattern detectable under light of infra-red wavelengths, but the patterns detectable under visible and infra-red light can also be present on different layers. The patterns detectable under the visible and IR wavelengths can each be any detectable pattern such as, for example, a cross-hatched pattern or another discernible shape. But any detectable pattern can be used. The layer containing the pattern detectable under visible light can also be the frangible layer, and thus more than one device can be present in a single layer of the label.

Another layer of the label can contain one or more taggant ink(s). The taggant ink(s) can be detectable under light of one or more uv wavelengths or range(s) of uv wavelengths, for example by an optical detection system. The layer can be arranged so that all or part of the taggant ink(s) is/are not visible as long as there is a layer covering the taggant ink (e.g., a tensioned layer). In some embodiments a taggant ink can be present that has a first detectable pattern when a tensioned layer is intact and a second pattern when the tensioned layer has been distorted. The second pattern can be simply a detectable change in the first pattern. In other embodiments one taggant ink can be detectable when the tensioned layer is intact and a second taggant ink detectable when the tensioned layer has been subjected to distortion. In one embodiment the taggant ink(s) can be printed on the underside of the covering layer, or can be a separate layer. But if the covering layer of the label is distorted the area of printed taggant ink is exposed or changed and such exposure or change becomes detectable under light of uv wavelengths.

The taggant ink can add important identifying characteristics to the assembly. For example in some embodiments the taggant ink can emit light at one or more emission wavelengths or ranges of wavelengths when illuminated by light of one or more excitation wavelengths or ranges of wavelengths. Particular wavelengths or ranges of wavelengths of the ink can be known to the manufacturer of the assembly and associated with the particular assembly. Thus in those embodiments where validation or authorization is to be communicated by a remote validator, the optical detection system of the user can communicate to the remote validator the wavelengths being emitted by the taggant ink. If these emitted wavelengths correspond to those known to be contained in the taggant ink of that assembly by the manufacturer, this is an indication of the presence of a valid assembly. In some embodiments the taggant ink can also have one or more RFID tags detectable at particular wavelength(s), which can also have identifying characteristics useful for this purpose. The identity of the assembly, for example lot number, can be easily ascertained by including on the assembly a barcode or other identifying number or device that is detectable by the instrument in a manner that can be read by the instrument. This information can also be transmitted to the remote validator and therefore the remote validator can correlate the specific wavelengths of light emitted from the device being validated with that information known about the device from the identification device. The remote validator therefore has further means to validate the assembly.

There can also be present a layer that is transparent and covers and protects all the other layers of the label, and assists adherence of the label to the assembly or to itself. In some embodiments this is the top layer of the label. In one embodiment the label of the invention therefore uses both mechanical and visual features to ensure label integrity and detect the presence or absence of tampering. A mechanical feature is one that is based on a physical change in the label.

Figure 2:
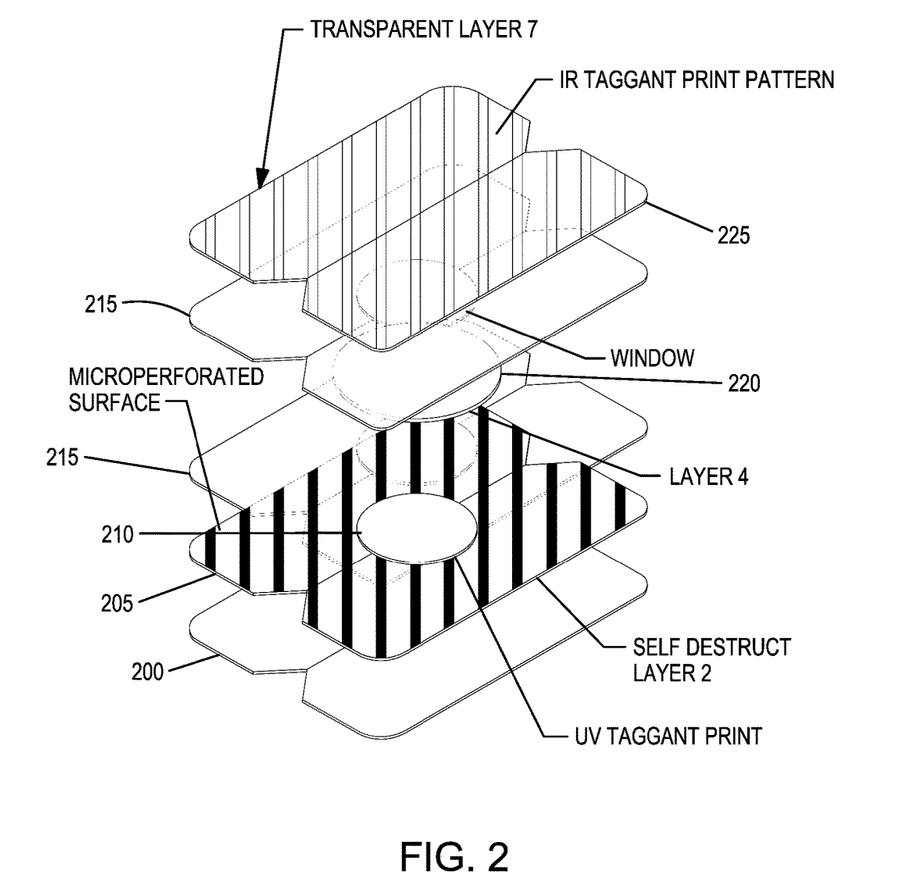
FIG. 2 provides an exploded view of a label of the invention.

An embodiment of a label of the invention is depicted in exploded view in FIG. 2. Layer 200 shows an adhesive layer for adhering the label to a surface of the cover and container and/or carrier. On top of layer 200 is layer 205, which is a frangible layer that also has a pattern that is detectable under light of a first wavelength or range of wavelengths (e.g., visible light) present on its surface. Layer 210 has an area having a taggant ink thereon that is detectable under light of a second (emission) wavelength or range of wavelengths (e.g., ultra-violet light). In this embodiment the taggant ink is printed on the layer. Layer 210 is covered by tensioned layer 220 so that when the label is intact taggant ink of layer 210 is not visible under light of excitation wavelength. If the label is distorted, which is very easily done under mechanical stress, then layer 210 becomes exposed and the ink will become detectable under the light of the second wavelength or range of wavelengths (e.g., ultra-violet light) by the detection system. Layers 215 are adhesive layers present for the purpose of holding the various layers together. Additional adhesive layers can also be present as part of the label (not all shown). Layer 220 covering layer 210 is a web of semi-elastic thermoplastic that is tensioned prior to lamination, or in other embodiments is a layer of metallic foil (e.g., aluminum or a similar metal) but in other embodiments (not shown) it can be cut in a shape to form tabs that cover a layer beneath it having the taggant ink. Layer 225 is a transparent layer that has a pattern printed on its underside that is detectable under light of a third wavelength or range of wavelengths (e.g., infra-red light). This layer ensures that a counterfeit layer cannot be placed over the label to mimic the pattern detectable under the light of the first wavelength or range of wavelengths (e.g., visible light) and thereby gain an unauthorized validation or authorization of the assembly, for example by a remote validator.

Inspection/Authorization Process and Use

The process utilized to inspect the label and gain validation or authorization, for example from a remote validator, can be varied. Validation refers to a process by which a clearance or authorization is obtained, which can allow the instrument to proceed with method steps. The method steps can be instructions or steps for performing an operation on the material within the assembly such as, for example, the assembly of a DNA molecule or performance of an assay or other biological procedure. The instructions can be software for performing an operation on the valuable material in the assembly, which instructions can be present as data within the instrument itself and accessed upon receipt of an authorization code, but in other embodiments the instructions are downloaded from the remote validator or a computer under the control of the remote validator. The remote validator is a computer or other electronic device that receives information from the instrument (directly or indirectly) seeking clearance or authorization and, after confirming that the assembly is a valid assembly communicates authorization (or the completion of validation) to the instrument, either directly or indirectly. The remote validator is not necessarily entirely electronic. It can also be under the control of a person that evaluates information communicated from the instrument (directly or indirectly) and it can be the person that takes an action communicating the authorization. The remote validator can receive validation information from the instrument seeking validation and analyze that information to determine whether or not authorization should occur. Validation information includes all information relating to the identity of the assembly and whether or not tampering with the assembly has occurred. In other embodiments validation and authorization is performed by the instrument seeking validation. In these embodiments the information necessary to validate the assembly is present within the instrument seeking validation or within a second instrument connected to the instrument seeking validation. The instrument seeking validation is therefore able to access information required to establish validation, whether through the internet to a remote validator or computer under the control of a remote validator, or whether to an instrument otherwise connected to the instrument seeking validation, or whether such information is contained within the instrument itself. If validation is achieved, it can similarly access information necessary to perform the appropriate operation on the valuable material in the container.

As an example, the process can involve placing the assembly in communication with an instrument that will validate the assembly and, in some embodiments, can also perform steps of accessing the material and performing appropriate method steps on the material. But the instrument can also be one that simply gathers validation information about the assembly. In a particular embodiment the instrument is a robotic gantry that performs a method using the valuable material within the assembly. In a particular embodiment the valuable material is a plurality of DNA molecules located in multiple wells of the container and the method is a series of steps for assembling a larger DNA molecule.

The method of validating and authorizing can involve different steps that confirm that no distortion has occurred in any of the plurality of devices contained in the label(s), and thereby detect the absence of tampering. Some or all of the steps can be performed by a detection system, for example an optical detection system. The process can contain steps of 1) activating light of one or more first (visible) wavelength(s) and determining the absence of distortion in a frangible layer of the label that has a specialized printed pattern—an absence of distortion in this layer of the label is taken to indicate that there has been no attempt to, for example, peel back the label and gain access to the valuable materials within the container (e.g., to remove or replace them); 2) activation of light of one or more second wavelength(s) (e.g., uv) to reveal an absence of detection of the presence of taggant ink—an absence of distortion or detection in this layer is taken to indicate that the covering layer is intact (referring to an absence of detectable distortion) and there has been no attempt to remove the layer covering the layer with the taggant ink; 3) activation of a light of one or more third (e.g., infra-red) wavelength(s) is performed to detect a pattern printed on the underside of a layer, which pattern is detectable under light of infra-red wavelength. An absence of distortion in this layer is taken to indicate that this layer has not been peeled off or removed and replaced with a counterfeit layer having the pattern detectable under visible light. Additional steps can be performed on additional layers that can be included in the label(s) until the necessary level of security has been met. These steps can be performed in any order. These steps can be performed by the same instrument that removes the cover and/or performs operations on the valuable materials inside the container, or by a separate instrument. The operations performed will depend on the nature of the valuable material and the purposes to which the invention is applied. In one embodiment the valuable material is a plurality of DNA molecules and the operations are steps for joining the plurality of DNA molecules to synthesize a larger DNA molecule.

The instrument performing the validation can do so in an automated fashion. The instrument can have various components for performing various steps. It can have a detection system, for example an optical detection system with the required hardware and software to perform necessary illuminations and detections of reflected wavelengths and patterns of light. In various embodiments the instrument can have components for performing the validation and authorization processes, but can also have components for receiving software instructions from an electronic device under the control of the remote validator, and can also have components for performing a series of operations on the material in the container, e.g., reactions for the joining of pieces of DNA.

In some embodiments the instrument performs steps of gathering validation information as described herein and transmits that validation information to a remote validator. The remote validator then analyzes the information and communicates validation or authorization (or the absence thereof) to the instrument, e.g., via the internet or other electronic communication. There can be one or more other instruments, or even persons, in between the instrument and the remote validator. In embodiments where the instrument performs steps on the material inside the container, a result of validation can mean the instrument is enabled to access programming for proceeding to perform said steps, for example by receiving an authorization code that unlocks the software. In some embodiments the programming steps for the operation can be downloaded from the remote validator or a computer under the control of the remote validator upon a result of validation or authorization. Conversely, a result of no validation or authorization will mean that the instrument is not enabled to access the programming for performing said steps, or that the remote validator does not allow a download of programming. Therefore, the steps can be performed only when a validated assembly is being used to perform the steps and authorization has been obtained by the instrument.

A detection system is any system, or electronic, or mechanical instrument that is able to detect distortion in one or more layers of the label. In one embodiment the detection system is an optical detection system. An optical detection system refers to various types of optical detectors that can find use in the invention in detecting distortion in one or more layers of the label. Such optical detection systems are known in the art and include, but are not limited to, photosensors or photodetectors that sense light or other electromagnetic energy. The system can therefore have a pattern recognition capability for recognizing patterns in the label(s) and detecting distortions in the label(s), for example by applying pattern recognition algorithms. The optical detection system can be of various types. Examples include (but are not limited to) an image sensor, such as those commonly used in small cameras, or a cryogenic detector that can measure emission of infrared photons, or an LED, or an optical detector that can detect photons, or a photoresistor, or a quantum dot photoconductor or photodiode, which detect wavelengths in the visible and infra-red wavelengths, a photodiode or photocathode that can detect light in the UV spectrum, or a photomultiplier device. Optical detection systems useful in the invention can involve the use of one or more various wavelengths of light illumination in conjunction with detection and/or a variety of image detection algorithms.

Tampering or Distortion

The label of the invention allows for the detection of the occurrence of tampering with the assembly. Tampering includes, but is not limited to, an attempt to remove all or part of a label and/or to dislodge a cover component from the assembly. The assembly is designed so that tampering will result in a detectable distortion of at least one layer of the label. Distortion refers to the result that one or more layers of the label is changed due to applied force, rather than retaining its cohesion as a single object. Distortion can be manifested as a fracturing or breaking or loss of material integrity of one or more layers of the label. Distortion can also include an absence of or failure of the detector to detect the presence of a device in a layer, and can also be the detection of a substance in or on the label, or a layer of the label (e.g., a taggant ink) that will be detectable if tampering has occurred. As an example distortion can be caused by an attempt to remove the label, such as by peeling or scraping it off or otherwise physically manipulating the label. The multiple layers of the label are designed to indicate such distortion in different ways, and to reveal distortion caused by different methods of tampering. The distortion is detectable by a detection system, such as an optical detection system. Other types of detection systems can also be utilized in the invention. The type of detection system utilized will depend on the plurality of devices incorporated into the label.

In some embodiments the valuable material can be fragments of DNA that, when joined in a particular order, make a larger desired sequence of DNA. This therefore exposes a potential that the fragments of DNA could be used to create a prohibited sequence of DNA, such as those that might be useable as instruments of bioterrorism. Therefore, in one embodiment the fragments of DNA comprised in the wells of the container can be placed randomly into the wells, meaning in an order that is unrelated to the order in which the fragments are to be assembled. The fragments can also be placed blindly into the wells of the container, meaning that the identity of a particular fragment in a particular well is unknown to the end user. In this embodiment the sequence of the fragments and/or the order of the fragments necessary to assemble the fragments into the larger desired sequence of DNA is known only to the party controlling the remote validator. The identity of a fragment and order of assembly is therefore contained in the software for performing the operation on the DNA or other valuable material. If, after performing the validation exercise, no tampering is detected and authorization is achieved, the programming steps for the series of steps for joining the DNA fragments can be downloaded as described herein. Since the sequence present in the specific wells of the container are not known to the party performing the DNA assembly reaction, the DNA fragments could not be used in an effort to utilize the DNA fragments to assemble a prohibited sequence.

In some embodiments one or more taggant inks can be included within one or more of the wells of the container. As part of validating an assembly there can be included steps of removing the one or more cover components and detecting the presence or absence of one or more taggant inks detectable at a specific wavelength in one or more of the individual compartments. As part of a method of manufacturing a tamper resistant assembly of the invention there can be included a step of placing within the one or more individual compartments of the container one or more taggant inks detectable at a specific wavelength. In these embodiments the taggant inks can be any as described herein.

The assemblies of the invention can therefore have a combination of taggant inks present within some of the wells or individual compartments of a container. As part of the validation the instrument can illuminate certain wells of the container with light of one or more specific wavelength(s) or range of wavelengths and detect emitted light at one or more specific emission wavelength(s) or range of wavelengths. The excitation and emission wavelengths used can correlate to the taggant inks known to be present in specific compartments. The particular excitation and emission wavelengths to be utilized by the instrument performing the validation and which individual compartments to be interrogated can be determined by the instrument from the barcode or other identifying number present on the assembly, as described herein, or can be downloaded from the remote validator. The response from the interrogation by illumination of the indicated individual compartments can then be transmitted to the remote validator as validation information and be considered as part of the validation procedure.

EXAMPLE 1

Validation of an Assembly

In this Example the valuable material in the container is fragments of DNA that are to be assembled into a larger piece of DNA. The instrument in this Example has an optical detection system that gathers validation information about the assembly. After communicating the information to a remote validator and gaining authorization the instrument downloads software containing a series of operations that the instrument will perform on the pieces of DNA present in the container of the assembly. The operations are instructions for performing a series of reactions for joining the pieces of DNA.

The assembly is placed in an indicated location on the instrument and the instrument is activated. Using the optical detection system the instrument performs the necessary steps of detection using three different types of illumination, which will reveal tampering (or the absence thereof) indicated by at least three of the layers of the label. This validation can be performed in stages, with each stage involving activation of a particular wavelength of light, e.g., UV, IR or visible light. This illumination protocol is performed with a label having three print patterns that are used to identify and validate it when the following steps are performed. This embodiment uses a label depicted in FIG. 2 described herein and the assembly has four such labels positioned so that each of the four is partially affixed to the cover piece and partially affixed to the carrier, which fits snugly into the container and thereby contains the pieces of DNA present in the wells of the container.

The first type of light that is activated is a light of visible (or broad spectrum) wavelength, which can be used to ensure that each security label has not been peeled up or removed and placed back into position. In this embodiment validation involves utilizing a combination of micro-perforations to form the frangible layer and specialized print patterns placed upon the same layer of the label (e.g., FIG. 2, 205). Any attempt to peel back the label will cause the layer to deflagrate into a number of different pieces, which will cause a distortion in the layer and in the pattern detectable under visible light. Such distortion would be detected by the optical detection system and would thus prevent validation of the assembly. Using illumination with light in the visible spectrum the pattern is detected as intact.

The optical detection system then proceeds and activates a light that illuminates the label with light of a second (uv) wavelength. The label is illuminated at the excitation wavelengths and detection performed at the emission wavelength. This detects any type of image that might occur in the area of the layer having ultra-violet taggant ink (210) that emits light of a particular emission wavelength when illuminated with light of appropriate excitation wavelength. Upon inspection this layer is found to not emit light at the emission wavelength, indicating that this layer of the label is also intact. If light is detected at the emission wavelength, this would be taken as an indication that distortion of the label has occurred causing the taggant ink to be detectable, and thus that tampering has occurred. But taggant ink is not detected.

The optical detection system proceeds and activates a light that illuminates the label with light of a third (infrared) wavelength, thus revealing the pattern detectable on the underside of layer 225 under light of infra-red wavelength. This ensures that a counterfeit layer printed with a pattern detectable under the light of the first (e.g., visible) wavelength as in layer 205 cannot be affixed on top of the label to camouflage any tampering that may have occurred. An attempt to apply such counterfeit layer would obscure the pattern present on the underside of layer 225 and result in a denial of validation of the assembly. The IR image is detected, which is taken as an indication that no tampering has occurred.

In this embodiment the identity of the assembly is determined from a barcode on the assembly and communicated to the remote validator. The remote validator accesses information to ascertain the wavelengths of light that should be detectable for that particular assembly under a range of excitation wavelengths. The instrument now proceeds to cut the label, which is performed by a component of the instrument and is done in an automated fashion. After cutting of the label the taggant ink is exposed to the optical detection system. The optical detection system then illuminates the label with light of a plurality of excitation wavelengths and detects light at a plurality of emission wavelengths. If no light is detected at one or more of the emission wavelengths this is taken as an indication that the assembly is counterfeit or has been tampered with because after cutting the label the taggant ink should be exposed and detectable. But light is detected at each expected emission wavelength, and this is taken as an indication that the assembly and has not been tampered with.

Since the above steps do not detect tampering or distortion of any layer of the label, the instrument communicates that information to the remote validator with the validation information about the assembly. The remote validator is a computer present at an installation under the control of the authorized provider of the assembly device. The remote computer of the authorized provider then processes the information and determines that the assembly is valid. It then communicates authorization to the instrument performing the validation exercise and the method that utilizes the valuable material contained in the assembly can proceed. The authorization can be communicated directly by the computer of the authorized provider, or can be communicated to another computer or device that provides the final validation and/or authorization. The computer of the authorized provider can also be programmed to transmit the instructions for performing a series of steps that utilize the valuable material, which in this embodiment includes instructions for performing a series of joining reactions on the pieces of DNA in the assembly.

What is claimed is:

1. A tamper resistant assembly that securely contains a valuable material comprising:
    a) a container for holding the valuable material and, optionally, a carrier comprising the container;
    b) one or more cover components that enclose(s) the valuable material in the container;
    c) one or more labels, each comprising a plurality of devices comprising a frangible layer, a pattern detectable under visible light, and a layer detectable under ultra violet light, that reveal tampering by distortion of at least one of the plurality of devices; and
    d) the one or more labels positioned so that dislodging one or more of the cover components causes the distortion of at least one of the plurality of devices, the distortion detectable by a detection system and thereby revealing tampering with the assembly.

2. The tamper resistant assembly of claim 1 wherein the label is affixed partially to a surface of a cover component, and partially to a surface of the container or to the optional carrier comprising the container.

3. The assembly of claim 1 wherein the distortion is detectable by a remote validator.

4. The assembly of claim 1 wherein the label comprises multiple layers, which comprise the plurality of devices.

5. The assembly of claim 1 wherein the layer detectable under ultra violet light comprises a device comprising a taggant ink detectable under ultra violet light.

6. The assembly of claim 2 wherein the assembly comprises a carrier that contains the container and the label is affixed partially to a surface of a cover component and partially to a surface of the carrier comprising the container.

7. The assembly of claim 5 wherein the taggant ink is detectable when said device comprising a taggant ink detectable under ultra-violet light is fractured.

8. The assembly of claim 4 wherein the frangible layer is distorted upon application of shear forces and further comprises a pattern detectable in visible light comprised on the frangible layer.

9. The assembly of claim 8 wherein the distortion comprises distortion of the pattern detectable under visible light.

10. The assembly of claim 4 wherein the label comprises a first layer that comprises the pattern detectable under visible light and a second layer comprising the pattern detectable under infra-red light, and the second layer is comprised on top of the first layer.

11. The assembly of claim 1 wherein one or more of the cover component(s) seals the valuable material in the container.

12. The assembly of claim 11 wherein the container comprises wells, and the valuable material is comprised in wells of the container, and one or more of the wells further comprise one or more taggant inks.

13. A method of detecting the occurrence of tampering with an assembly of claim 1 containing a valuable material, comprising:
    a) analyzing the assembly with a detection system; and
    b) detecting the presence or absence of distortion in one or more of the plurality of devices and thereby detecting whether tampering with the assembly has occurred.

14. A tamper resistant assembly that securely contains a valuable material comprising:
    a) a container for holding the valuable material and, optionally, a carrier comprising the container;

b) one or more cover components that enclose(s) the valuable material in the container;
c) one or more labels, each comprising a plurality of devices comprising a frangible layer, a pattern detectable under infra-red light, and a layer detectable under ultra violet light, that reveal tampering by distortion of at least one of the plurality of devices; and
d) the one or more labels positioned so that dislodging one or more of the cover components causes the distortion of at least one of the plurality of devices, the distortion detectable by a detection system and thereby revealing tampering with the assembly.

15. The tamper resistant assembly of claim 14 wherein the label is affixed partially to a surface of a cover component, and partially to a surface of the container or to the optional carrier comprising the container.

16. The assembly of claim 14 wherein the distortion is detectable by a remote validator.

17. The assembly of claim 14 wherein the layer detectable under ultra violet light comprises a device comprising a taggant ink detectable under ultra violet light.

18. The assembly of claim 15 wherein the assembly comprises a carrier that contains the container and the label is affixed partially to a surface of a cover component and partially to a surface of the carrier comprising the container.

19. The assembly of claim 17 wherein the taggant ink is detectable when said device comprising a taggant ink detectable under ultra-violet light is fractured.

20. The assembly of claim 14 wherein the label comprises a first layer that comprises the pattern detectable under visible light and a second layer detectable under ultra-violet light, and the second layer is comprised on top of the first layer.

21. The assembly of claim 14 wherein the container comprises wells, and the valuable material is comprised in wells of the container, and one or more of the wells further comprise one or more taggant inks.

22. A method of detecting the occurrence of tampering with an assembly of claim 14 containing a valuable material, comprising:
a) analyzing the assembly with a detection system; and
b) detecting the presence or absence of distortion in one or more of the plurality of devices and thereby detecting whether tampering with the assembly has occurred.

23. A tamper resistant assembly that securely contains a valuable material comprising:
a) a container for holding the valuable material and, optionally, a carrier comprising the container;
b) one or more cover components that enclose(s) the valuable material in the container;
c) one or more labels, each comprising a plurality of devices comprising a pattern detectable under visible light, a pattern detectable under infra-red light, and a layer detectable under ultra violet light, that reveal tampering by distortion of at least one of the plurality of devices; and
d) the one or more labels positioned so that dislodging one or more of the cover components causes the distortion of at least one of the plurality of devices, the distortion detectable by a detection system and thereby revealing tampering with the assembly.

24. The tamper resistant assembly of claim 23 wherein the label is affixed partially to a surface of a cover component, and partially to a surface of the container or to the optional carrier comprising the container.

25. The assembly of claim 23 wherein the distortion is detectable by a remote validator.

26. The assembly of claim 23 wherein the layer detectable under ultra violet light comprises a device comprising a taggant ink detectable under ultra violet light.

27. The assembly of claim 24 wherein the assembly comprises a carrier that contains the container and the label is affixed partially to a surface of a cover component and partially to a surface of the carrier comprising the container.

28. The assembly of claim 26 wherein the taggant ink is detectable when said device comprising a taggant ink detectable under ultra-violet light is fractured.

29. The assembly of claim 23 wherein the label comprises a first layer that comprises the pattern detectable under visible light and a second layer detectable under ultra-violet light, and the second layer is comprised on top of the first layer.

30. The assembly of claim 23 wherein the container comprises wells, and the valuable material is comprised in wells of the container, and one or more of the wells further comprise one or more taggant inks.

31. A method of detecting the occurrence of tampering with an assembly of claim 23 containing a valuable material, comprising:
a) analyzing the assembly with a detection system; and
b) detecting the presence or absence of distortion in one or more of the plurality of devices and thereby detecting whether tampering with the assembly has occurred.

* * * * *